United States Patent
Bahr

(10) Patent No.: US 10,525,174 B2
(45) Date of Patent: Jan. 7, 2020

(54) PIMPLE PULLER

(71) Applicant: Rex Romaine Bahr, Portland, OR (US)

(72) Inventor: Rex Romaine Bahr, Portland, OR (US)

( * ) Notice: Subject to any disclaimer, the term of this patent is extended or adjusted under 35 U.S.C. 154(b) by 0 days.

(21) Appl. No.: 14/491,917

(22) Filed: Sep. 19, 2014

(65) Prior Publication Data

US 2015/0080667 A1  Mar. 19, 2015

Related U.S. Application Data

(60) Provisional application No. 61/879,692, filed on Sep. 19, 2013.

(51) Int. Cl.
*A61M 1/00* (2006.01)

(52) U.S. Cl.
CPC ....... *A61M 1/0023* (2013.01); *A61M 2202/06* (2013.01); *A61M 2210/04* (2013.01)

(58) Field of Classification Search
CPC ............ A61M 1/0047; A61M 2210/04; A61M 1/0023; A61M 2202/06; A61B 19/5202
See application file for complete search history.

(56) References Cited

U.S. PATENT DOCUMENTS

| | | | | |
|---|---|---|---|---|
| 5,676,635 A * | 10/1997 | Levin | ................... | A61B 1/2676 600/120 |
| 5,776,119 A * | 7/1998 | Bilbo | ................... | A61M 1/0023 604/317 |
| 6,102,885 A * | 8/2000 | Bass | ................... | A61B 18/1482 604/22 |
| 2003/0095781 A1* | 5/2003 | Williams | ............... | A61B 17/02 385/146 |
| 2005/0154381 A1* | 7/2005 | Altshuler | ............. | A61B 18/203 606/9 |
| 2008/0228103 A1* | 9/2008 | Ritchie | ............. | A61B 10/0275 600/563 |
| 2009/0234176 A1* | 9/2009 | Lebovic | ............... | A61N 5/1016 600/6 |
| 2013/0046316 A1* | 2/2013 | Sullivan | ............. | A61B 10/0275 606/115 |
| 2013/0116612 A1* | 5/2013 | Stephan | ................... | A61N 5/06 602/43 |

* cited by examiner

*Primary Examiner* — Tatyana Zalukaeva
*Assistant Examiner* — Sara A Sass
(74) *Attorney, Agent, or Firm* — Michael L. Greenberg, Esq.; Greenberg & Lieberman, LLC

(57) ABSTRACT

A vacuum powered 'pimple puller' configured to extract pus and other biomaterial from within an individual's or animal's clogged pore with mild suction provided by an external vacuum source, which is channeled through the body of the present invention. The force of the vacuum is focused on the target area of skin by one of a variety of applicator tips designed to be affixed to the head of the present invention while in use. It is the intent of the present invention to successfully remove biomaterial from a pore by rupturing the skin's surface, while minimizing the risk of infection.

5 Claims, 5 Drawing Sheets

PIMPLE PULLER

CONTINUITY

This application is a non-provisional application of provisional application No. 61/879,692, filed on Sep. 19, 2013, and priority is claimed thereto.

FIELD OF THE PRESENT INVENTION

A handheld device with a conical, removable tip, configured to utilize suction generated from an external and mild vacuum source, in order to remove detriment from an animal or human's pores, including, but not limited to pimples caused by acne, blackheads, or boils. The present invention maintains a vacuum in a cylindrical handle located in a lateral chamber above the battery cell, which is preferably used by a trained professional to remove detriment from pores in an animal's or individual's skin, which are illuminated during extraction by a built in lamp.

BACKGROUND OF THE PRESENT INVENTION

Unfortunately, similar to dental hygiene, taking care of one's skin can be a dangerous, difficult, laborious, and even painful task. Teenagers and even some adults are plagued with acne related skin issues, often causing red bumps, pimples, blackheads, whiteheads, or other pus-filled skin protrusions. The recommended avenue to resolve these skin blemishes is to remain patient, waiting for the pimple or blackhead to pop or recede on its own. However, this is rarely the case. It is far more common for a person to get impatient with the healing process, and attempt to pop or deflate the pimple or other blemish far before the healing process is completed. This is disadvantageous due to the increased risk of infection created by a forced break in the skin's surface, releasing contaminants that could spread an infection. Squeezing a pimple can force the bacteria-containing fluids through the layers of the surrounding skin, facilitating the spread of infection. Additionally, pimples should not be deliberately popped because of the increased risk of creating a visible scar through the break in the skin. Despite these reasons, it is fairly common for individuals to get impatient with the natural, slow healing process of these skin issues, and to simply pop the protrusion deliberately in order to relieve the swelling and pain, or simply for aesthetics reasons.

Unfortunately, many times when individuals attempt to do this, the condition is often worsened. The area surrounding the condition becomes red from skin irritation due to the violent skin popping, be it through squeezing the protrusion, or through pushing down on it with the hand or other blackhead removal tools. If there were a simple way in which individuals or animals could have their skin protrusions popped, or to have the often painful pressure within them released, while minimizing the risk of infection, relief could be experienced, and the healing process of these skin issues could be expedited.

Thus, there is a need for a device that could safely and easily extract detriment from an individual's or animal's pores, providing relief of the pressure, without exasperating the condition and spreading the infection.

SUMMARY OF THE PRESENT INVENTION

The present invention, a hand-held, illuminated pimple puller, configured to extract biomaterial debris from an individual's or animal's clogged pores by means of a mild vacuum force, provided via an external vacuum source. The vacuum is focused within the head of the present invention, and is routed to the opening located at the end of the conical applicator tip, which is pressed against the clogged pore requiring cleaning. It is the intent of the present invention to remove biomaterial such as pus from within a pore on an individual's or animal's skin through the use of a pinpointed or focused vacuum, which gently breaks the skin if need be via suction, and in some cases the skin to be lanced/cut to facilitate, pulling the material out of the pore, and into the head of the present invention. In some cases, the protrusion may require cleaning and/or a brief lancing or puncturing prior to using the present invention. The present invention is designed such that it fits firmly in the hand of a trained professional, and is equipped with several features which facilitate the controlled use of the device.

The preferred embodiment of the present invention is equipped with an illuminated viewing window, framed with an optional magnifying glass, which provides a direct viewing channel through the head of the device, allowing the operator to successfully place the tip of the present invention over the target skin protrusion. During use, the present invention is pressed firmly against the skin's surface, creating an airtight seal. The head of the present invention is angled at an obtuse angle, providing additional leverage against the skin, as well as ensuring the target skin area is visible through the viewing window when in the proper position. After being placed into position over the skin protrusion, the operator preferably places his or her thumb over the vacuum control hole located on the top portion of the present invention. The vacuum control hole may be located elsewhere, such as on the side of the present invention. A vacuum is to be continuously pulled through the device, and the control hole has to be left open until the device is firmly in place on the desired location. This allows the vacuum force channeled through the vacuum hose to flow freely into the head of the present invention, after the control hole is plugged, the vacuum will pull on the surface of the skin, and thus, the skin protrusion. Once the vacuum is strengthened via the removal of air from the present invention to a sufficient extent, where the suction can be felt against the skin, the operator may gently pull the present invention away from the skin while the suction is in effect, and the skin protrusion will ideally rupture. The rupture may cause pus and other liquid biomass to be sucked into the head of the present invention through the applicator tip. The present invention has a filter that is preferably in the shape of a small rectangle which slides into the head in front of the opening to the handle. The filter is to be replaced often via disassembly of the present invention. In the event that the present invention is used on a blackhead, the blackhead will be extracted rather than significant amounts of pus. The head of the present invention is designed such that it is easy to disassemble for cleaning and sterilization after each use. Additionally, numerous applicator tips of varying size have been fashioned to address an assortment of problems. Extra large applicator tips are available for use on megafauna, such as elephants or other large animals as well. The interchangeable applicator tips are secured by a conventional interlocking twist-clasp or a slip-on design, which locks the tip in place on the head, and seals the vacuum with an air-tight flexible washer, ensuring that the vacuum force remains consistent once applied to the skin.

The preferred body of the present invention is crafted of an easy-to-clean material such as stainless steel, or bacteria-resistant plastics, facilitating sanitation of the present invention. The battery compartment, located at the rear of the present invention, near the vacuum hose connector, is preferably sealed with an o-ring or other airtight seal, ensuring that debris does not contaminate the battery compartment. The preferred body of the present invention is preferably not capable of being sanitized by microwaves due to the metal in the light fixture, as well as the bulb; however, hot water, steam, or an autoclave may be alternately used to sanitize the present invention. The battery serves to power the guiding light, which illuminates the target area via an angled directional mirror within the head, which angles the light downward, into the conical applicator tip, and onto the target.

DETAILED DESCRIPTION OF THE PREFERRED EMBODIMENT OF THE PRESENT INVENTION

Figure 1:
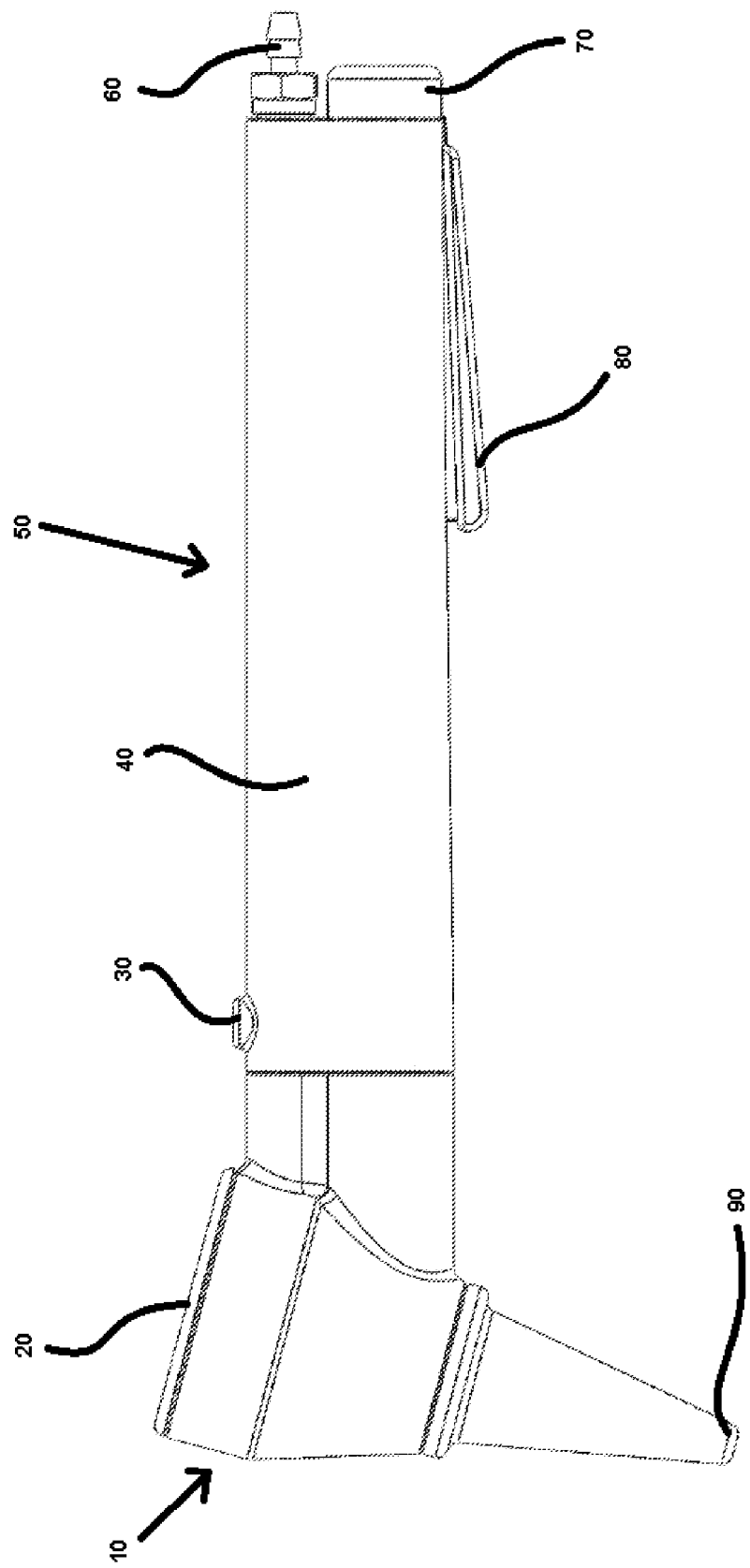
FIG. 1 displays the external portion of the present invention from the side.
Figure 2:
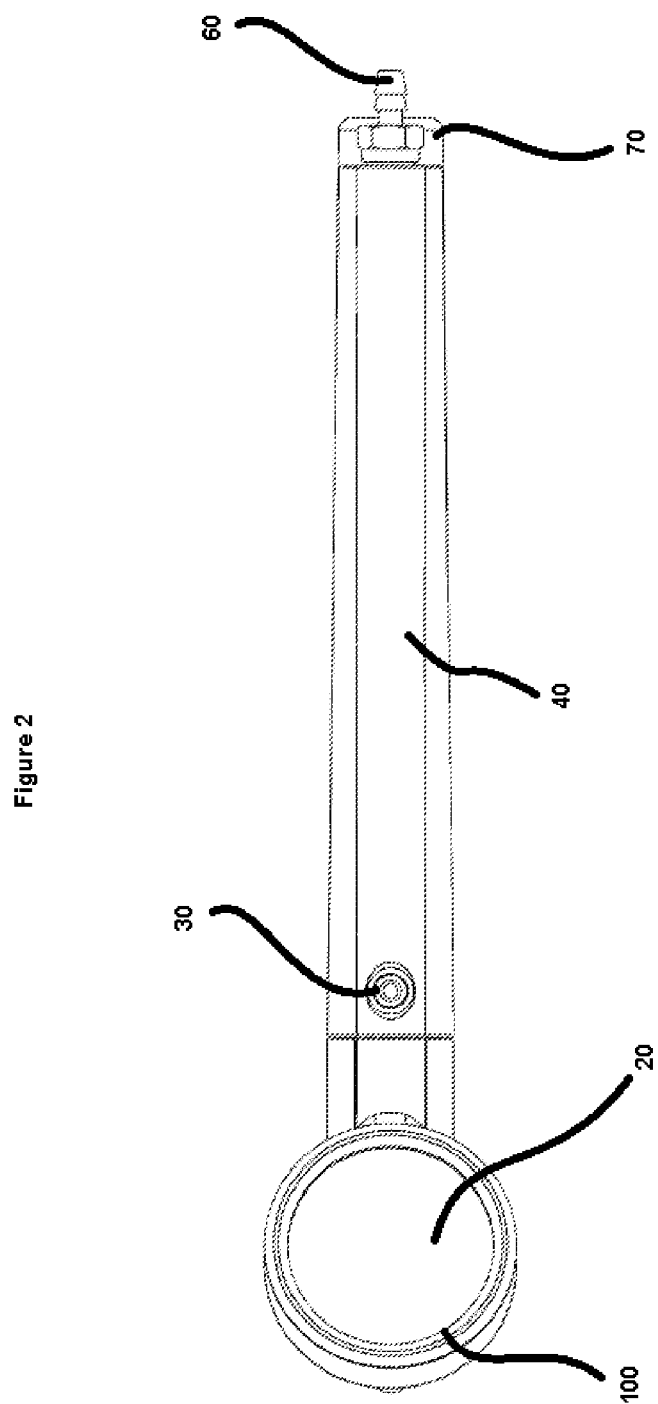
FIG. 2 exhibits the present invention as viewed from above, while the unit is in use.

The preferred embodiment of the present invention is configured to remove fluidic biomaterial from an individual's or animal's clogged skin pore with the force of suction, provided by an external conventional vacuum pump. It is designed to effectively extract pus and other biomaterial from beneath the skin's surface, such as pimples, blackheads, and whiteheads by means of a conical applicator tip (90), which focuses the suction of the vacuum at a single point, which is then firmly placed over the target skin protrusion when in use. It is the intent of the present invention to minimize the risk of spreading an infection while easily relieving the pressure and discomfort associated with a skin protrusion such as a zit or pimple.

The present invention is preferably configured with an angled head (10), a body (50), and an applicator tip (90), all of which function together to channel the vacuum towards the skin protrusion requiring treatment. The head (10) is set at an obtuse angle to facilitate leverage against the skin by the operator, as slight pressure against the skin is required to form a vacuum seal. The head (10) is equipped with an illuminated viewing window (20) which is used by the operator to guide the present invention to the target area requiring treatment. The illuminated viewing window (20) is easily replaceable or removable for cleaning. An optional replaceable magnifying lens (100) may be used to enlarge the target area of skin, facilitating the operator's ability to see the targeted area through the viewing lens, and ensure he or she is on target. The head (10) of the present invention may also be easily removed for cleaning and sterilization.

The head (10) of the present invention is also configured to accept a variety of conical applicator tips (90), which are similar to those used by doctors to view inside of an individual's ear. These applicator tips (90) are affixed to the head of the present invention with a secure interlocking twist clasp at the juncture between the head (10) and the applicator tip (90). The applicator tip is fastened with the aide of a small flexible washer, which helps to create an airtight seal, ensuring vacuum suction is not degraded by any substantial gaps in the system. The applicator tip (90) functions to pinpoint the power of the vacuum over the target area of skin, providing a firm seal around the pimple or other protrusion.

Alternate embodiments of the present invention provide for the head (10) to be removable to facilitate sterilization in a microwave for subsequent patients. Additionally, the present invention is preferably equipped with a removable filter located in the head, designed to prevent biomaterial and debris from being drawn or sucked into the handle. In some models of the present invention, the head (10) is to be disposable and discarded as need be.

Figure 3:
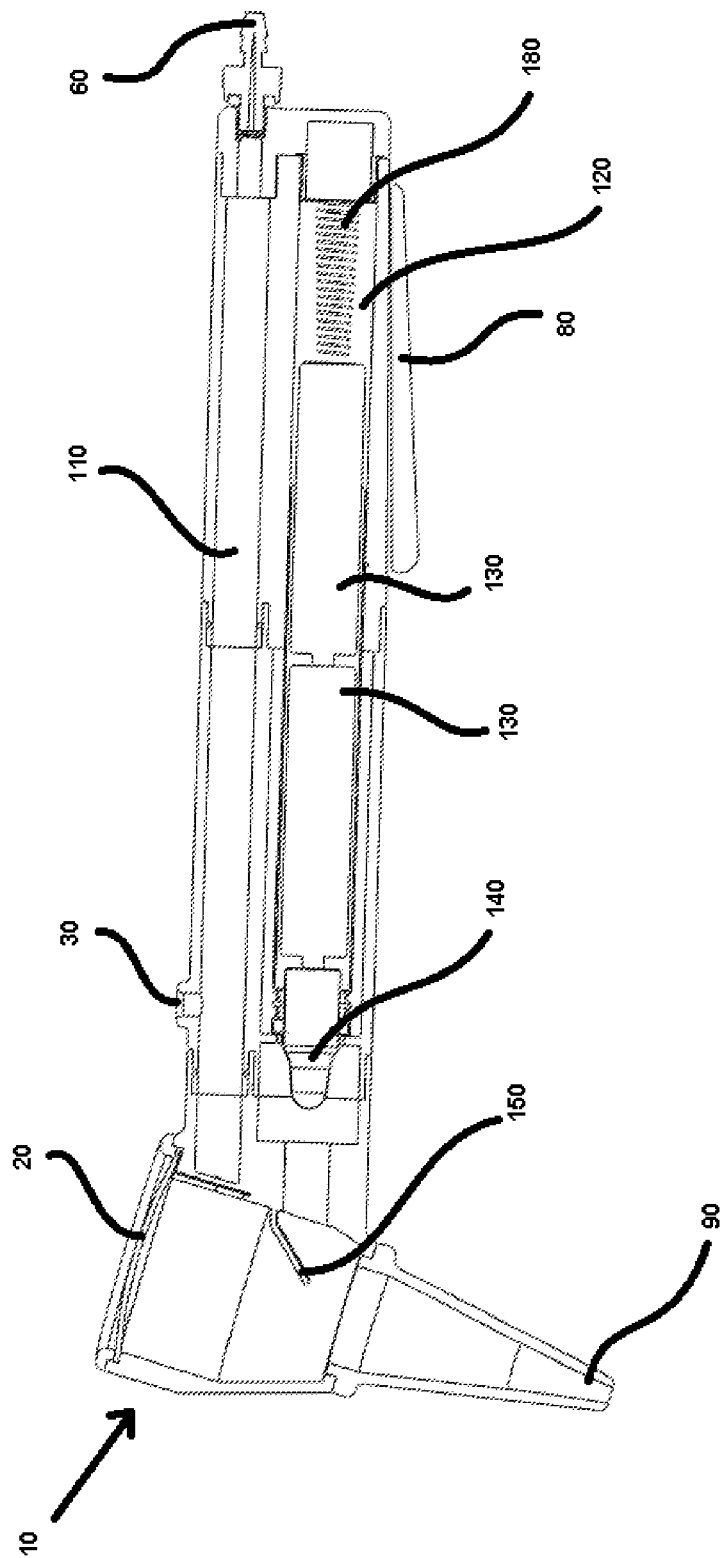
FIG. 3 is a cross-sectional view of the present invention from the side.
Figure 4:
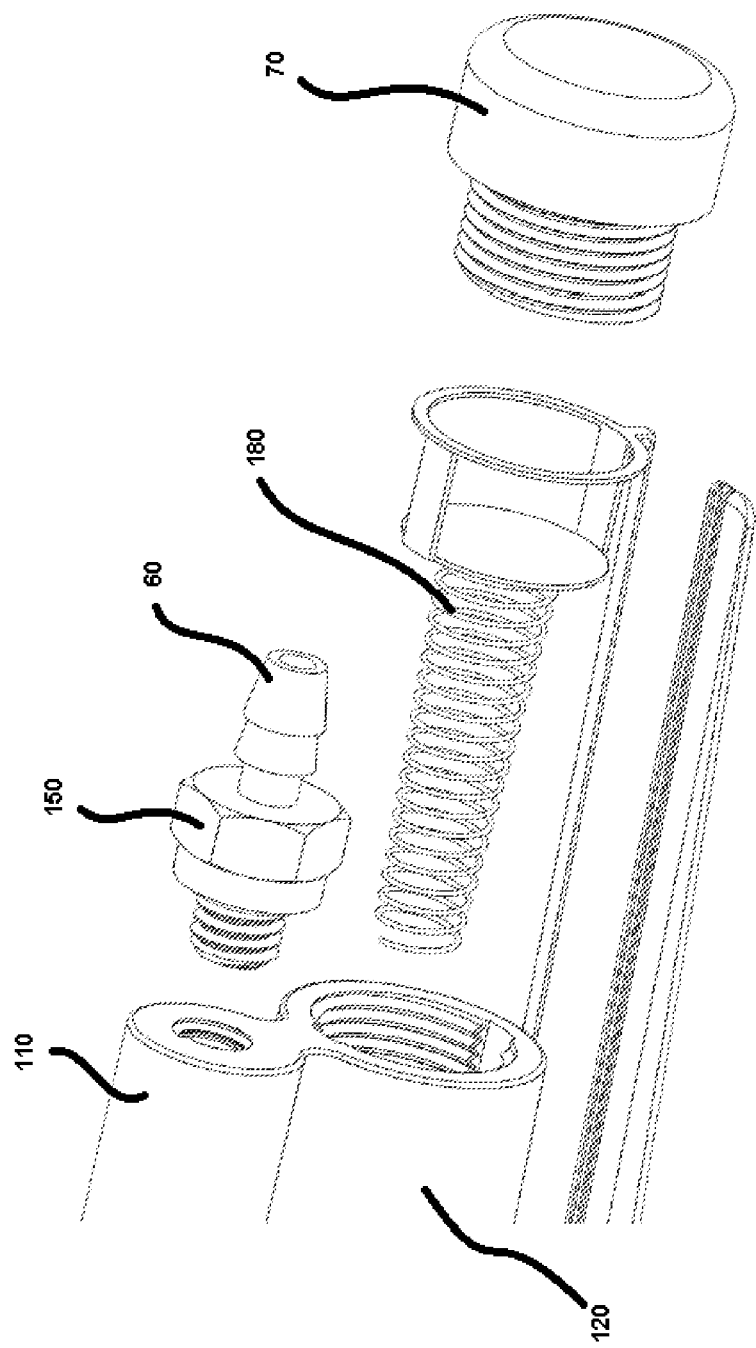
FIG. 4 highlights the battery compartment and vacuum tube connector.
Figure 5:
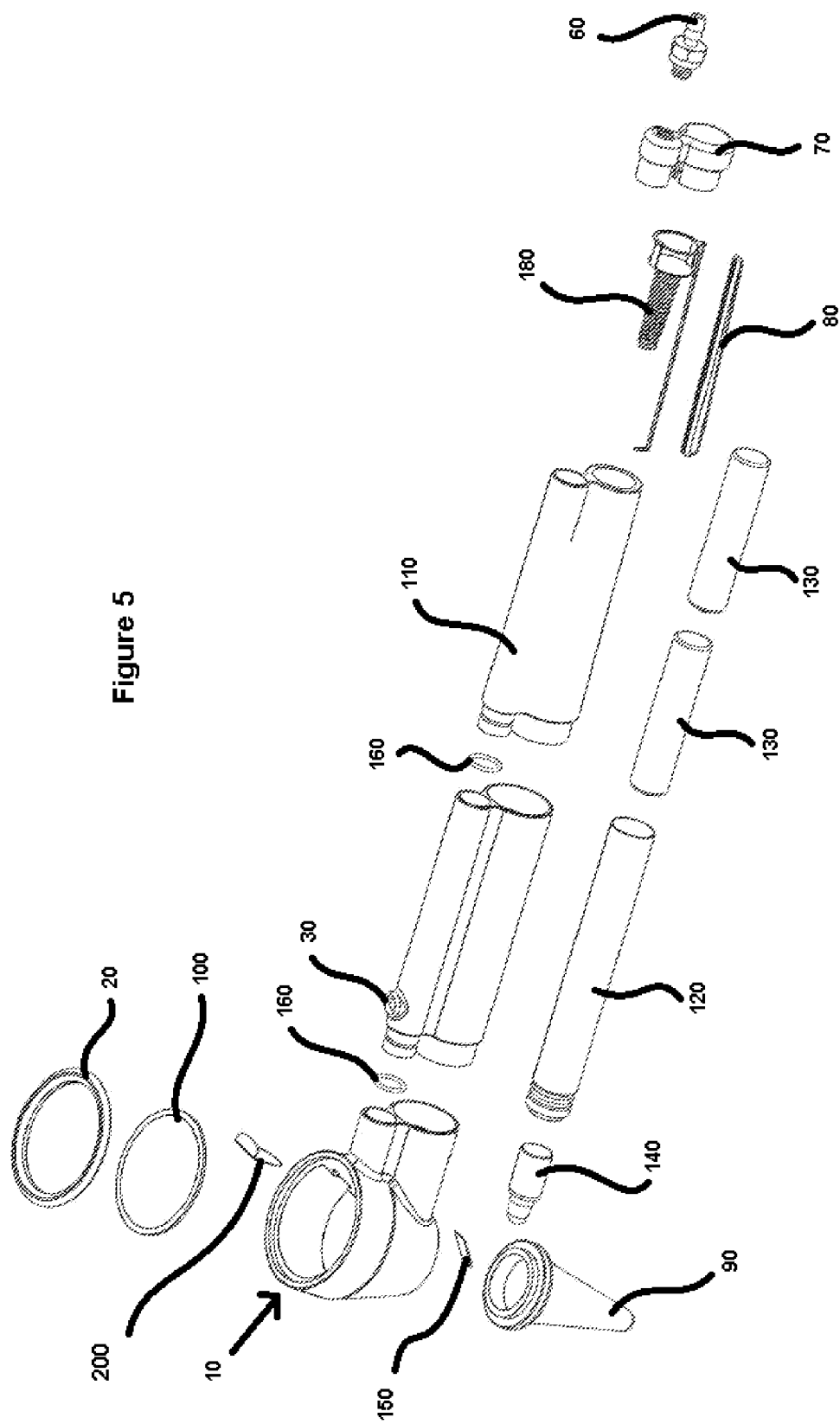
FIG. 5 shows the present invention disassembled, from the side.

The body (50) of the present invention is designed to fit comfortably in one hand, leaving the operator's second hand free to stabilize or flatten the skin surrounding the target. It is configured with a battery compartment (120) with space for two AA or AAA batteries (130), which are held in place with a conventional tension spring (180) as seen in FIG. 3. The battery compartment is sealed closed with a battery compartment cap (70), which is augmented by a small rubber o-ring or soft washer, ensuring contaminants do not enter the battery compartment (120). The batteries function to power the light bulb (140), providing light to the present invention, which is channeled into the head (10) of the present invention with the aide of a small angled conventional mirror (150). The mirror is angled at approximately 45 degrees in order to direct the light down into the applicator tip (90), illuminating the target area through the hole at the narrow point of the applicator tip (90).

Additionally, within the body (50) of the present invention, there lies a vacuum chamber (110) through which the vacuum force is channeled. The vacuum chamber (110) functions to carry the suction provided by the external vacuum pump through the vacuum hose connector (60), through the body (50) of the present invention, and finally into the head (10), whereupon it is used to remove detriment from a clogged pore via mild suction and expert handling of the present invention. This process is detailed below. The vacuum hose connector (60) is preferably positioned at the rear of the present invention as seen in FIG. 3, and unscrews from the present invention for cleaning or maintenance.

The present invention is preferably intended to be used by a trained professional, such as a dermatologist, doctor, barber, registered nurse, C.N.A Nurse assistant, or acupuncturist. The operator should be wearing gloves while using the present invention, in order to curb the risk of infection posed by a break in the skin's surface. A latex or similarly disposable glove also assists in securing vacuum suction through the use of the vacuum control valve (30), which is located at the top of the handle, and is designed to be regulated by the operator's thumb while the present invention is in use. In order to successfully remove an unwanted or uncomfortable skin protrusion, the operator would connect the conventional vacuum pump to the present invention via a small flexible hose, which is firmly fastened to the vacuum hose connector (60) at the rear of the present invention, just above the battery cap, as seen in FIG. 1, and turn the pump on. The vacuum is then channeled down the vacuum chamber (110). However, while the present invention is not in contact with the target region of skin, the operator will not employ the vacuum control valve (30), which will cause a break in the seal of the vacuum chamber (110), ensuring the vacuum does not enter and begin to build within the head (10) nor the applicator tip (90) until the present invention is placed into position over the target, and the operator is prepared to redirect suction to the skin.

When the qualified operator and patient are ready to begin, the operator will affix the appropriately sized applicator tip (90) to the head (10) of the present invention by twisting the applicator tip (90) into place securely. Next, the operator will grasp the present invention by the grip (40) firmly, using the pinky finger and ring finger to activate the light switch (80) preferably found along the bottom of the grip (40). The light switch (80) completes the circuit connecting the two batteries (130) to the light bulb (140) found within the grip (40) as seen in FIG. 3. Once the light switch (80) is activated, the small mirror (150) found within the head (10) of the present invention directs the illuminating light downward, into the conical applicator tip (90), illuminating the target area of skin, and facilitating accurate placement of the present invention over the target. The operator then guides the present invention over the target area of skin afflicted with the protrusion, ensuring that the exposed hole in the applicator tip (90) is placed squarely over the pimple or other skin protrusion, such that the center of the pimple is aligned with the center of the exposed hole in the applicator tip (90). The operator is aided in this task by the illuminated viewing window (20) found at the top of the head (10), providing a line of sight to the target through the present invention's head (10) and applicator tip (90). Once the applicator tip (90) of the present invention is firmly in place over the skin, the operator will place his or her thumb over the vacuum control valve (30) found along the top of the present invention, as seen in FIG. 1. The force of the vacuum is then channeled into the head (10) and applicator tip (90) of the present invention, and begins to build up against the surface of the skin. After a few seconds, sufficient pressure has been established within the present invention, which can be evidenced by the operator as the applicator tip (90) will remain attached to the skin without much additional pressure. Finally, the operator pulls the present invention slowly away from the skin at a direct angle perpendicular to the skin's surface. This creates the effect of a stronger vacuum while simultaneously compressing the skin slightly within the narrow portion of the applicator tip (90).

In most scenarios, the surface of the skin is ruptured, and the detriment buildup within the pore is suctioned out and off of the skin's surface, and into the applicator tip (90). After the extraction is complete, the operator will then clean the surface of the skin, and sanitize and change to a clean tip or a different type for future use on other patients. When finished with each patient, the head (10) is preferably dipped in a sanitizing solution before continuing to the next patient. It is advisable to have one or two units of the present invention for each qualified operator, which are preferably locked or secured when the operator is not actively on the job. The applicator tip (90) may then be disposed of or sanitized to prepare for the next patient, depending on the type of applicator tip (90), namely either disposable, or reusable.

Applicator tips (90) are preferably crafted by contracted manufacturers, given that their essential design is already in conventional use on a doctor's otoscope, and are designed in a variety of shapes and sizes to accommodate a wide assortment of skin protrusions. Applicator tips (90) that are extra large are placed over the top of a smaller applicator tip (90) in order to accommodate appropriate skin conditions on large animals. More expensive applicator tips (90) may be constructed out of a transparent resin, which would facilitate the operator's use of the present invention. Transparent applicator tips (90) would allow light originating from the light bulb (140) to radiate over a larger portion of skin, rather than only through the exposed opening in the applicator tip (90). Additionally, larger applicator tips (90) need not have a larger exposed opening, but may rather maintain a more elongated cone, which is prudent in scenarios where the target is recessed or difficult to reach.

An alternate embodiment of the present invention could include the use of pyramid-shaped applicator tips (90) rather than conical ones. Pyramid-shaped applicator tips (90) could be instrumental to addressing deeper skin conditions, which may require more direct points of the focused vacuum than the evenly allocated vacuum provided by the circular and conical applicator tips (90). It is also conceived that a more economical version of the present invention could be fabricated that excludes the light fixture of the present invention, thus decreasing manufacturing costs.

An additional alternate embodiment of the present invention could maintain a small vacuum pump within the grip (40) of the present invention, eliminating the need for an external vacuum source. This could be implemented into the body (50) of the present invention, near the end, and could potentially be powered by additional internal batteries (130), or similarly powered by a hand or foot operated vacuum pump. This would drastically increase the portability of the present invention, providing for the potential for the present invention to be used at home, or by a doctor making house calls to an individual's home. A more portable version of the present invention would also enable the present invention to be used outdoors, such as on remote zoo animals away from the veterinarian's office or for the military.

In one alternate embodiment of the present invention, an intake of an internal combustion engine could provide the primary vacuum source.

Another alternate embodiment of the present invention could be a mere variation on the intention of use. For example, the present invention could easily be modified with specialized applicator tips (90) or a small hose or tube that c an tolerate the vacuum to function as a device designed to extract nearly any small object from within an individual's person, such as shrapnel or any small, non-magnetic object. Objects could be extracted from an individual's eyeball, skin, or even an internal organ, such as a kidney with a specially modified applicator tip (90). In the event that the object is metal, a conventional magnet would likely be used instead of the present invention. However, it can be envisioned that a magnet assembly could be added to the present invention to facilitate the removal of magnetic objects from within a person or animal.

An alternate method of use for the present invention could include placing the applicator tip on the target area of skin prior to placing the tip of the head (10) into the applicator tip (90) while placed on the target, then placing the thumb onto the vacuum control valve (30). The vacuum control valve (30) may be held closed when the head (10) is placed onto the applicator tip (90) already applied to the target, as this provides the user with good control and an instant vacuum force applied to the target.

Another alternate embodiment of the present invention includes an alternate design of the vacuum control valve (30) of the present invention that employs a finger operated trigger switch rather than the established vacuum control valve (30) of the body (50) of the present invention designed merely to be covered with the finger of the operator. The finger operated trigger varies from that of the vacuum control valve (30) employed in the preferred embodiment of the present invention in that a physical switch is employed to cover the vacuum control valve (30) rather that the finger of the operator. This alternate embodiment of the present invention reduces the exposure of the operator, despite the fact that the operator should always wear gloves when operating any embodiment of the present invention.

Similarly, it should be understood that in alternative embodiments of the present invention, any components of the present invention, the body (50), head (10), and/or the applicator tips (90) may maintain additional patterns, colors, and even small plastic cosmetic pieces designed for cosmetic purposes only. For example, the body (10) may have small plastic flowers affixed to the grip (40), or the head (10) molded in the form of an animal, in order to make the present invention appear friendlier to children.

Additionally, alternate embodiments of the present invention could employ special, proprietary tips rather than the applicator tips (90) referred to in this disclosure. These special tips could be used for cleaning cavities on the human body, such as the ear or nose. Likewise, other embodiments of the present invention could be configured to aid in the extraction of shrapnel, bullets, or other metallic debris from a body via suction channeled through a specially shaped applicator tip (90).

Likewise, it is envisioned that alternate embodiments of the present invention may employ a laser in addition to or in lieu of the light bulb (140) in order to further facilitate guidance of the device over the target area. The laser is preferably mounted within the head (10) of the present invention, and is used by the trained user to acquire the target swiftly and accurately.

It is understood that the present invention is not solely limited to the invention as described in the embodiments above, but further comprises any and all embodiments within the scope of the this application.

I claim:

1. A device for removing fluidic biomaterial from a surface of a skin pore of an individual via a vacuum system comprising:
   a body that is elongate, said body having a first cylinder and a second cylinder, said first cylinder and said second cylinder joined and parallel to one another such that said first cylinder is disposed atop said second cylinder when held during use;
   said body equipped with a battery housing that is said second cylinder, a vacuum chamber that is said first cylinder, a handle that comprises said first cylinder and said second cylinder, a front end, and a rear end;
   a vacuum inlet, said vacuum inlet disposed at said rear end of said body;
   wherein said vacuum inlet is configured to receive a vacuum hose;
   two 1.5 v batteries, said two 1.5 v batteries disposed within said battery housing;
   wherein said battery housing is disposed at a bottom of said body;
   a head, said head disposed at said front end of said body;
   a circular opening, said circular opening disposed at a top of said head;
   wherein said head is angled at an obtuse angle from the top of said first cylinder towards said bottom of said body such that said head points down and extends down below said second cylinder;
   wherein said head is hollow;
   wherein said vacuum chamber is hollow;
   a round viewing window, said round viewing window disposed within said circular opening on said top of said head and is tilted with respect to said handle from a longitudinal axis of said handle;
   a magnifying lens, said magnifying lens disposed directly under said round viewing window;
   at least one light bulb, said at least one light bulb disposed at said front of said body, in front of said battery housing, in communication with said two 1.5 v batteries;
   at least one seal, said at least one seal present between said body and said head;
   a battery compartment cap, said battery compartment cap equipped with a tension spring disposed in communication with said two 1.5 v batteries;
   wherein said battery compartment is threaded;
   wherein said battery compartment cap is configured to screw into said battery compartment to ensure battery connection retention;
   a mirror, said mirror disposed within said head, in front of said at least one light bulb;
   wherein said mirror is angled at 45 degrees from said second cylinder and positioned inline with said second cylinder;
   an applicator tip, said applicator tip disposed at a bottom of said head, such that said at least one light bulb is under said first cylinder, between said first cylinder and said applicator tip;
   wherein said mirror is configured to direct light from said at least one light bulb towards said applicator tip;
   wherein said applicator tip is cone-shaped, approaching a point at a bottom of said applicator tip;
   wherein said handle is disposed along the same horizontal axis as said vacuum chamber of said body;
   a vacuum control valve, said vacuum control valve disposed on said top of said body;
   wherein said vacuum control valve is a hole to be blocked by the user when vacuum suction is needed;
   wherein said vacuum chamber channels the vacuum of the vacuum system from said vacuum hose inlet, through said body, into said head, and through said applicator tip upon blocking said vacuum control valve;
   a filter, said filter disposed within a filter receptacle within said head; and
   wherein said filter prevents the fluidic biomaterial from entering the vacuum chamber during use.

2. The apparatus of claim 1, wherein said head is removable for sterilization.

3. The apparatus of claim 2, wherein said applicator tip is disposable.

4. The apparatus of claim 3, wherein said applicator tip is transparent.

5. The apparatus of claim 4, wherein said viewing window presents a direct line-of-sight through said applicator tip to the skin pore.

* * * * *